United States Patent
Hanley et al.

(10) Patent No.: US 9,289,262 B2
(45) Date of Patent: Mar. 22, 2016

(54) DIELECTRIC COATINGS FOR LASER FIBER AND RELATED METHODS

(75) Inventors: Brian M. Hanley, Framingham, MA (US); Jessica Hixon, Watertown, MA (US); Christopher L. Oskin, Grafton, MA (US); Edward Sinofsky, Dennis, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1903 days.

(21) Appl. No.: 12/370,185

(22) Filed: Feb. 12, 2009

(65) Prior Publication Data
US 2009/0287198 A1  Nov. 19, 2009

Related U.S. Application Data

(60) Provisional application No. 61/054,278, filed on May 19, 2008.

(51) Int. Cl.
*A61B 18/24* (2006.01)
*G02B 6/26* (2006.01)
*A61B 18/22* (2006.01)

(52) U.S. Cl.
CPC .............. *A61B 18/24* (2013.01); *G02B 6/262* (2013.01); *A61B 2018/2205* (2013.01); *A61B 2018/2244* (2013.01); *A61B 2018/2277* (2013.01); *Y10T 29/49817* (2015.01)

(58) Field of Classification Search
CPC .................................. G02B 6/00; A61B 18/20
See application file for complete search history.

(56) References Cited

U.S. PATENT DOCUMENTS

| | | | |
|---|---|---|---|
| 5,163,935 A | 11/1992 | Black et al. | |
| 5,242,438 A | 9/1993 | Saadatmanesh et al. | |
| 5,354,294 A * | 10/1994 | Chou | 606/16 |
| 5,428,699 A | 6/1995 | Pon | |
| 5,431,647 A | 7/1995 | Purcell, Jr. et al. | |
| 5,437,660 A | 8/1995 | Johnson et al. | |

(Continued)

FOREIGN PATENT DOCUMENTS

| | | |
|---|---|---|
| DE | 94 13 311 U1 | 10/1994 |
| EP | 0 400 802 A2 | 12/1990 |

(Continued)

OTHER PUBLICATIONS

International Search Report and Written Opinion for International Application No. PCT/US2009/040491, mailed Jul. 23, 2009, 15 pages.

*Primary Examiner* — Lynsey Crandall
(74) *Attorney, Agent, or Firm* — Bookoff McAndrews, PLLC

(57) ABSTRACT

A method and an apparatus according to an embodiment includes a distal end portion of an optical fiber core having a multilayer dielectric coating. For side-firing optical fibers, the coating can be disposed on an angled surface at the core distal end to produce total internal reflection of laser energy at the angled surface. The coating can also be disposed on an outer surface of the distal end portion of the core. The coating and the angled surface can be collectively configured to redirect laser energy in a lateral or side-fired direction. For end-firing optical fibers, the coating can be disposed on an outer surface of the distal end portion of the core. The coating and a perpendicular surface at the core distal end can be collectively configured to direct laser energy in a direction substantially parallel to the distal end portion of the optical fiber.

13 Claims, 14 Drawing Sheets

(56) References Cited

U.S. PATENT DOCUMENTS

| | | |
|---|---|---|
| 5,509,917 A | 4/1996 | Cecchetti et al. |
| 5,537,499 A | 7/1996 | Brekke |
| 5,649,924 A | 7/1997 | Everett et al. |
| 5,772,657 A | 6/1998 | Hmelar et al. |
| 5,833,683 A | 11/1998 | Fuller et al. |
| 6,096,028 A | 8/2000 | Bahmanyar et al. |
| 6,179,830 B1 | 1/2001 | Kokubu |
| 6,296,608 B1 | 10/2001 | Daniels et al. |
| 6,361,530 B1 | 3/2002 | Mersch |
| 6,445,939 B1 | 9/2002 | Swanson et al. |
| 6,565,555 B1 | 5/2003 | Ryan et al. |
| 6,615,072 B1 | 9/2003 | Izatt et al. |
| 6,891,984 B2 | 5/2005 | Petersen et al. |
| 7,108,692 B2 | 9/2006 | Frenz et al. |
| 7,169,140 B1 | 1/2007 | Kume |
| 2005/0165315 A1 | 7/2005 | Zuluaga et al. |
| 2005/0259934 A1 | 11/2005 | Temelkuran et al. |
| 2006/0282068 A1 | 12/2006 | Griffin et al. |
| 2007/0179485 A1* | 8/2007 | Yeik et al. ............... 606/15 |

FOREIGN PATENT DOCUMENTS

| | | |
|---|---|---|
| EP | 0 610 991 A2 | 8/1994 |
| WO | WO 2007/112196 A2 | 10/2007 |

* cited by examiner

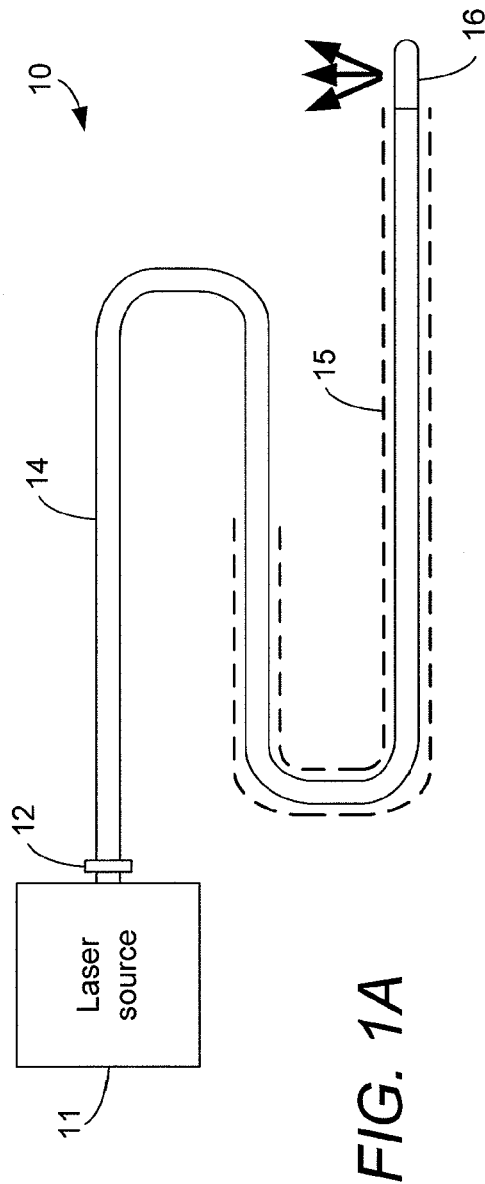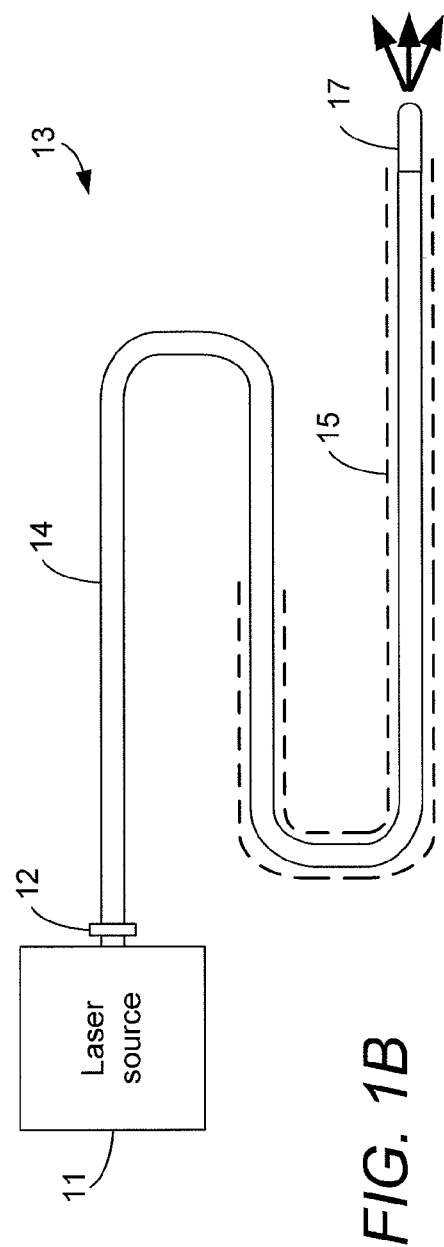
FIG. 1A
FIG. 1B

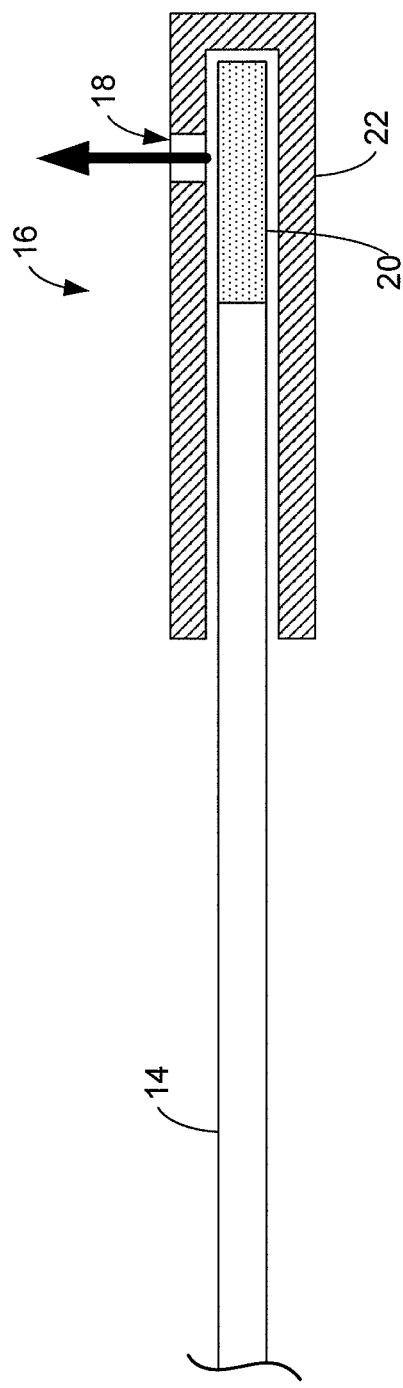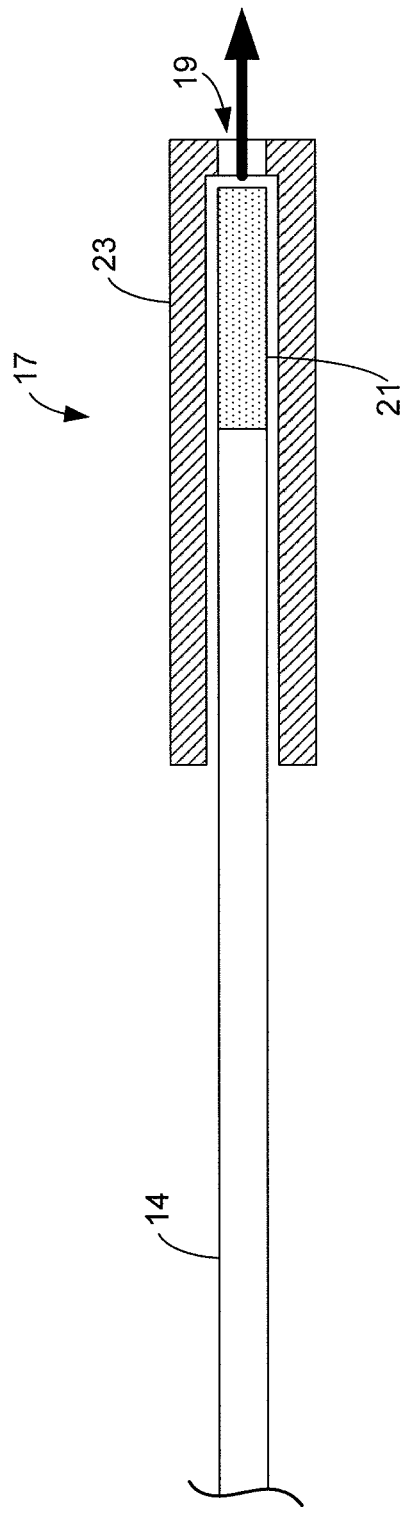

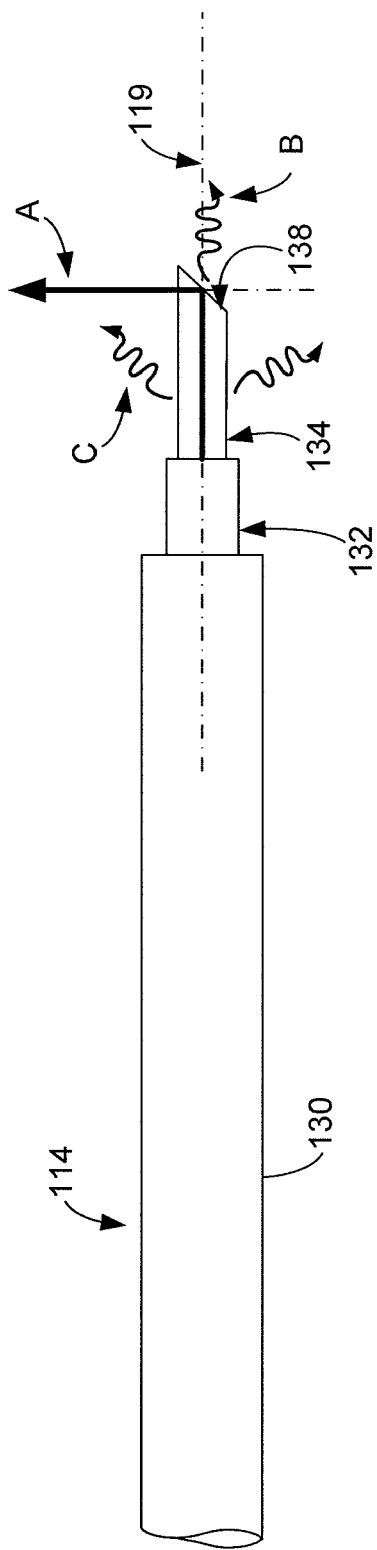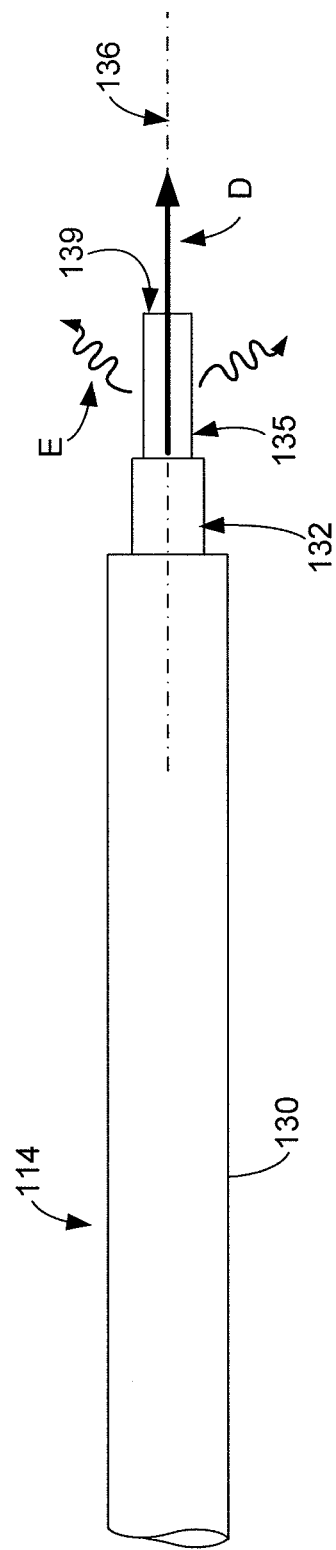

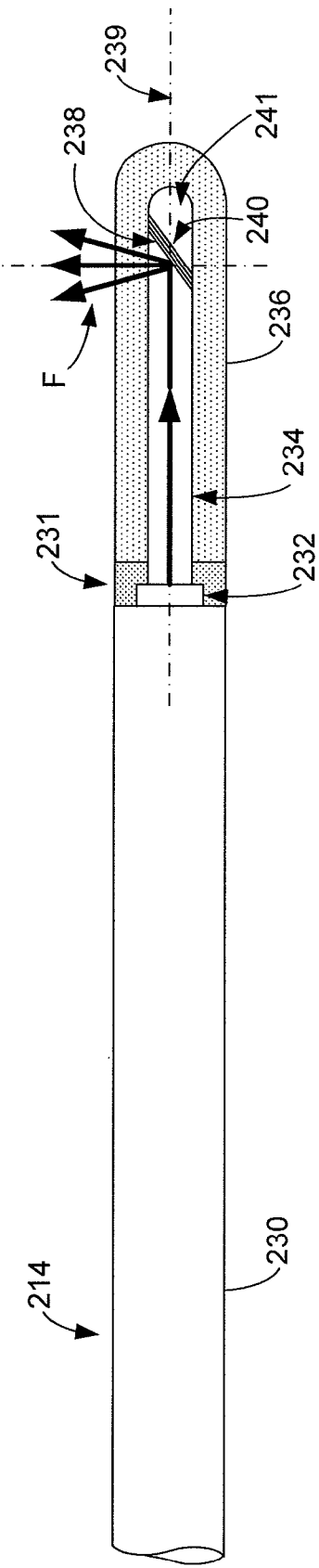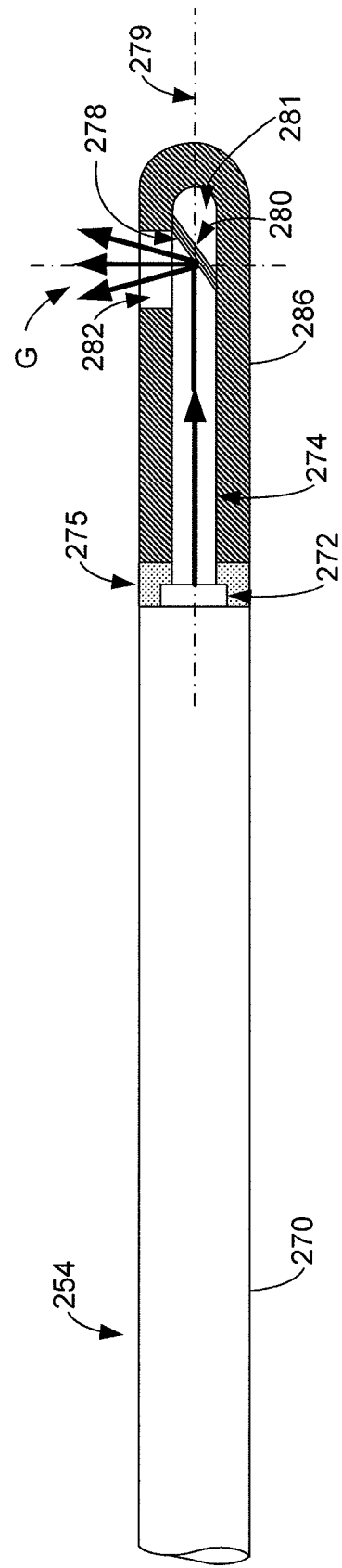
FIG. 4A
FIG. 4B

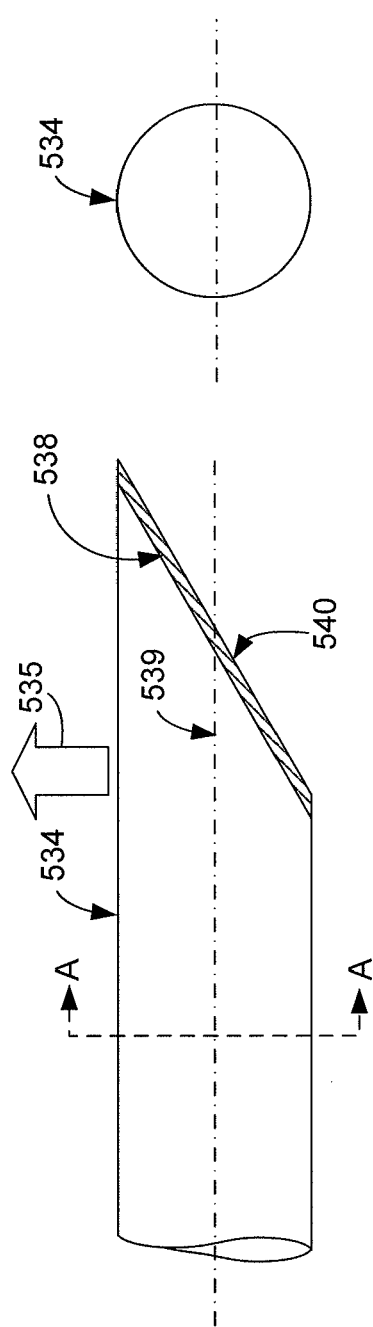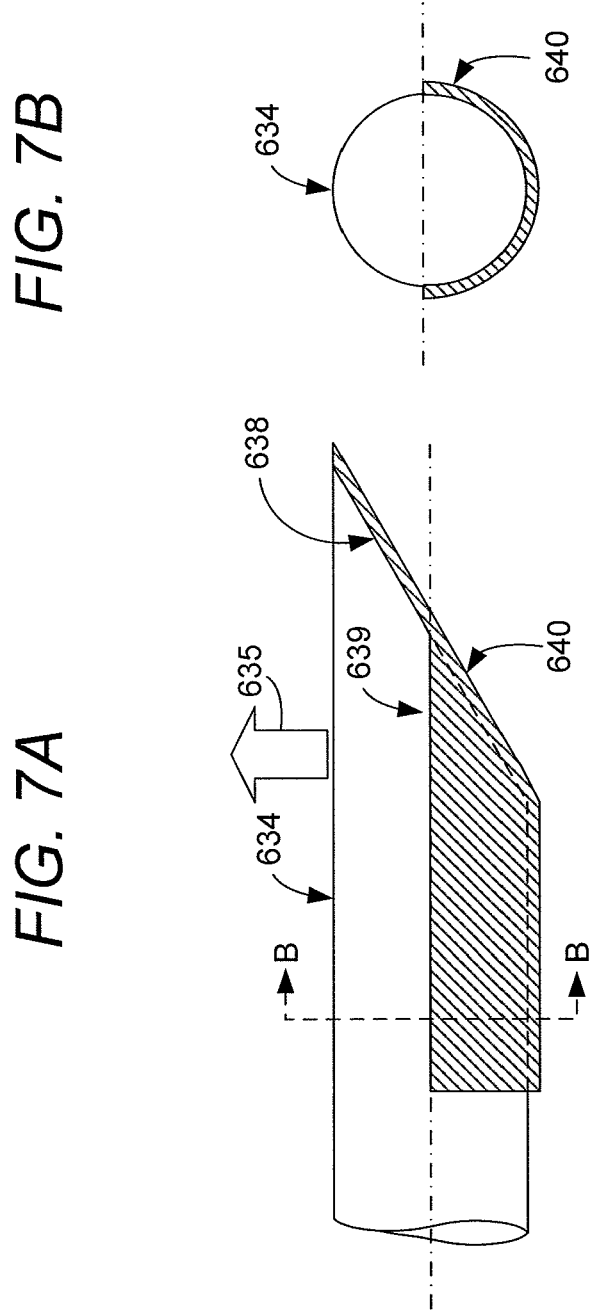

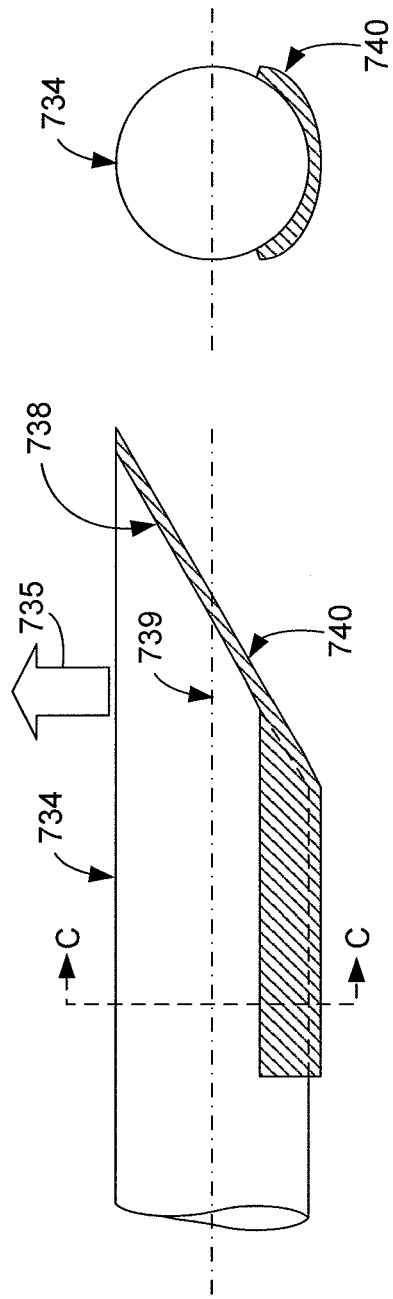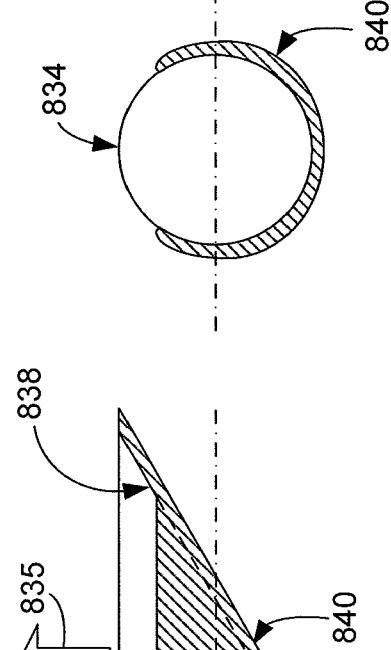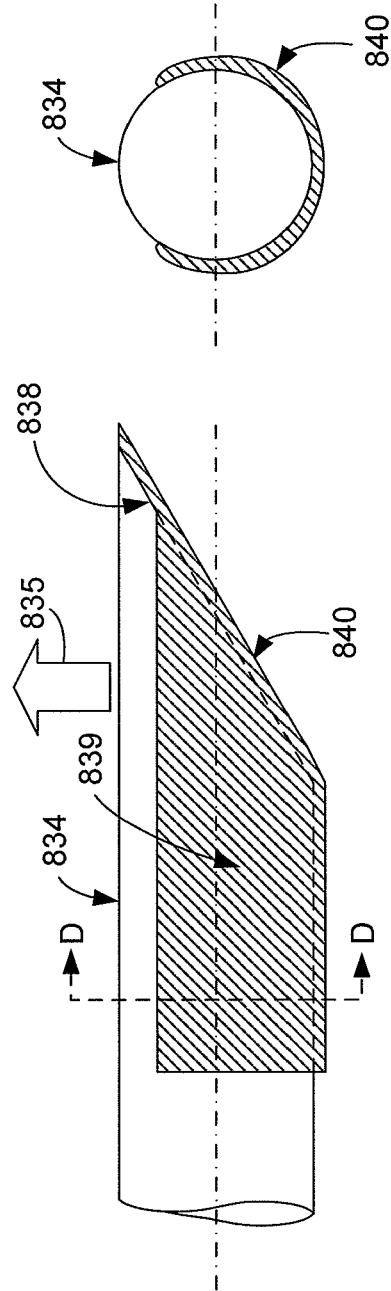

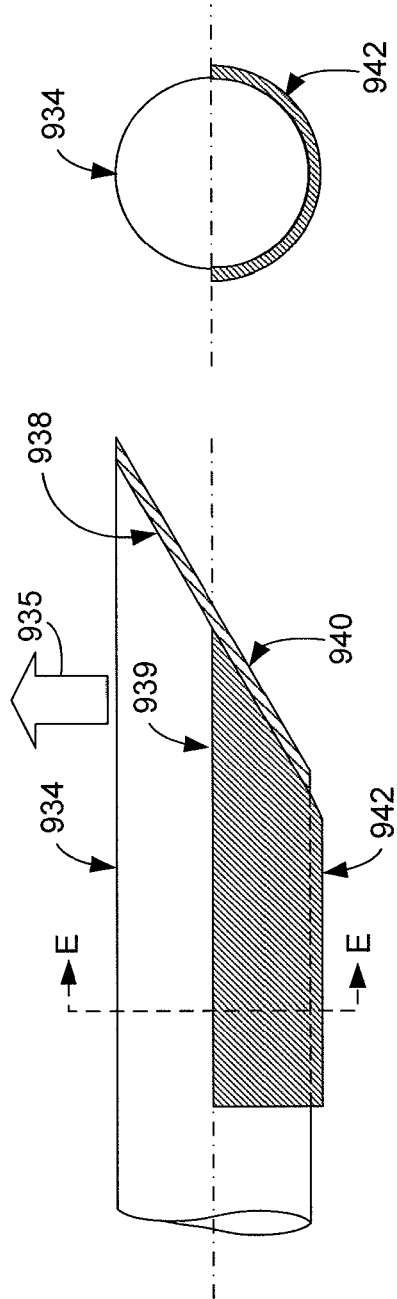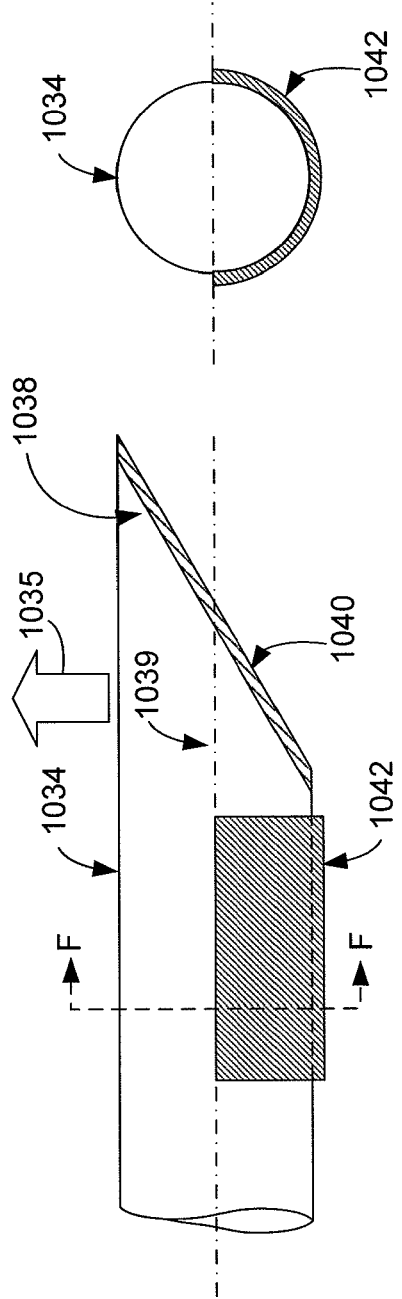

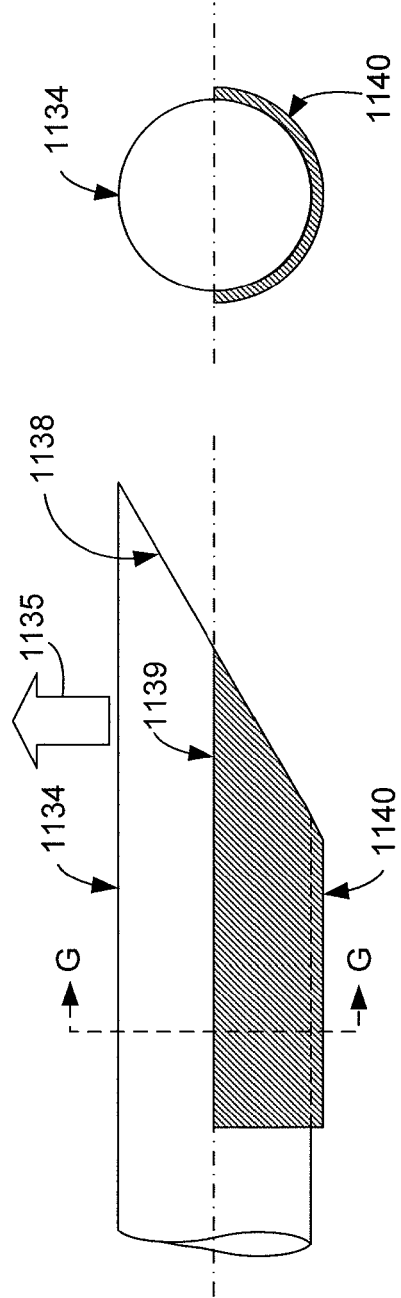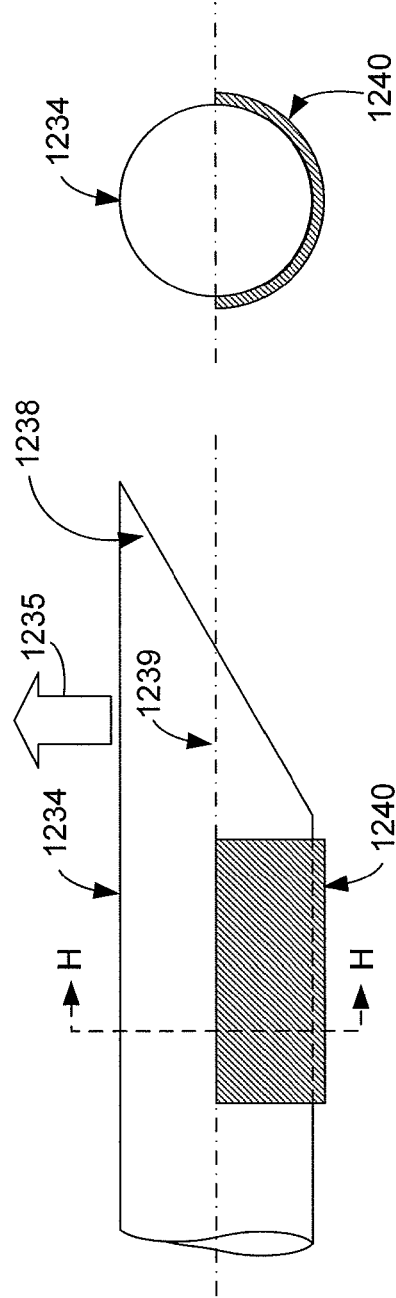

DIELECTRIC COATINGS FOR LASER FIBER AND RELATED METHODS

RELATED APPLICATION

This application claims priority to and the benefit of U.S. Provisional Application No. 61/054,278, filed on May 19, 2008, entitled "Dielectric Coatings for Total-Internal-Reflection Surface of Laser Fiber and Related Methods," which is incorporated herein by reference in its entirety.

BACKGROUND

Embodiments relate generally to medical devices and more particularly to side-firing and end-firing optical fibers and methods for using such devices.

Laser-based surgical procedures using an optical fiber can provide a medical practitioner with more control when applying laser energy to the appropriate treatment area. The optical fiber can be a side-firing optical fiber or an end-firing optical fiber based on the type of surgical procedure. Passing the distal end portion of the optical fiber through an endoscope during surgery, however, may damage, scratch, degrade, and/or deform the distal end portion of the optical fiber. To protect the optical-fiber end portion a capillary and/or a metal cap or cannula, usually made of surgical grade stainless steel, can be placed over the optical-fiber end portion. Once the optical-fiber end portion is properly positioned for treatment, the laser energy can be applied to the target area.

During use of the device, a portion of the laser energy can leak from the optical fiber end reducing the laser energy delivered to the treatment area and/or increasing overheating of the metal cap that is typically used to protect the optical fiber. Cooling of the device may be needed to operate at a safe temperature. In some instances, the overheating that can occur from the laser energy leakage can affect the mechanical and/or optical properties of the of the optical-fiber end portion, the capillary and/or the metal cap. In other instances, the overheating that can occur from the laser energy leakage can be sufficiently severe to damage the optical-fiber end portion, the capillary and/or the metal cap.

Overheating can also occur from the use of reflectors such as metallic reflectors or tips configured to redirect or bend an optical beam about 90 degrees from its original propagation path based on total internal reflection (TIR). Because metallic reflectors do not reflect 100% of the optical beam, the energy associated with the non-reflected portion of the optical beam can be absorbed by the metallic reflector and the metallic reflector can self heat. For TIR-based tips, a portion of the optical beam can leak through and heat up a protective metal cap positioned on a distal end of the tip. Furthermore, the glass capillary tubing that is generally used on the TIR-based tips can become damaged as tissue is ablated and impacts against the glass capillary tubing.

Thus, a need exists for optical fiber end portions that can increase side-fired and end-fired laser energy, increase device longevity, increase transmission efficiency, reduce overheating, and/or increase patient safety.

SUMMARY

A method and an apparatus according to an embodiment includes a distal end portion of an optical fiber core having a multilayer dielectric coating. For side-firing optical fibers, the multilayer dielectric coating can be disposed on an angled surface at the core distal end to produce total internal reflection of laser energy at the angled surface. The multilayer dielectric coating can also be disposed on an outer surface of the distal end portion of the core. The multilayer dielectric coating and the angled surface can be collectively configured to redirect laser energy in a lateral or side-fired direction. For end-firing optical fibers, the multilayer dielectric coating can be disposed on an outer surface of the distal end portion of the core. The multilayer dielectric coating and a perpendicular surface at the core distal end can be collectively configured to direct laser energy in a direction substantially parallel to the distal end portion of the optical fiber.

BRIEF DESCRIPTION OF THE DRAWINGS

FIGS. 1A-1B are schematic representations of an optical fiber side-firing and end-firing system, according to embodiments.

FIGS. 2A-2B are cross-sectional views of side-firing and end-firing optical fibers, according to embodiments.

FIGS. 3A-3B are side views illustrating laser energy leakage that may occur in side-firing and end-firing optical fibers.

FIG. 4A is a cross-sectional view of a side-firing optical fiber with a capillary, according to an embodiment.

FIG. 4B is a cross-sectional view of a side-firing optical fiber with a capillary, according to another embodiment.

FIG. 7A is a side view of a coated core-end surface, according to an embodiment.

FIG. 7B is an end view taken along line A-A of FIG. 7A.

FIG. 8A is a side view of a coated core end portion and a coated core-end surface, according to an embodiment.

FIG. 8B is an end view taken along line B-B of FIG. 8A.

FIG. 9A is a side view of a coated core end portion and a coated core-end surface, according to another embodiment.

FIG. 9B is an end view taken along line C-C of FIG. 9A.

FIG. 10A is a side view of a coated core end portion and a coated core-end surface, according to another embodiment.

FIG. 10B is an end view taken along line D-D of FIG. 10A.

FIG. 11A is a side view of a core end portion having a first multilayer dielectric coating and a core-end surface having a second multilayer dielectric coating, according to an embodiment.

FIG. 11B is an end view taken along line E-E of FIG. 11A.

FIG. 12A is a side view of a core end portion having a first multilayer dielectric coating and a core-end surface having a second multilayer dielectric coating, according to another embodiment.

FIG. 12B is an end view taken along line F-F of FIG. 12A.

FIG. 13A is a side view of a coated core end portion and a core-end surface, according to an embodiment.

FIG. 13B is an end view taken along line G-G of FIG. 13A.

FIG. 14A is a side view of a coated core end portion and a core-end surface, according to another embodiment.

FIG. 14B is an end view taken along line H-H of FIG. 14A.

DETAILED DESCRIPTION

Figure 5:
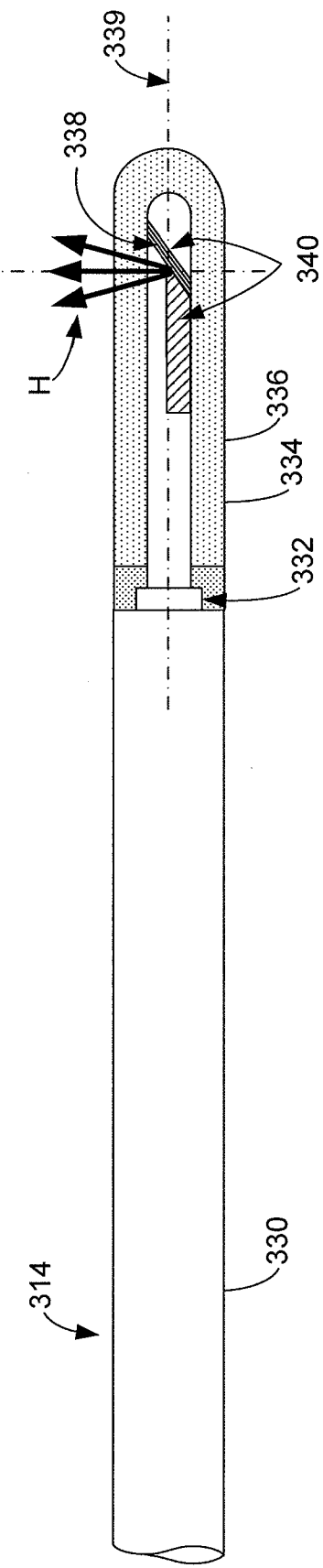
FIG. 5 is a cross-sectional view of a side-firing optical fibers with a capillary, according to another embodiment.

The devices and methods described herein are generally related to the use of side-firing optical fibers and end-firing optical fibers within the body of a patient. For example, the devices and methods can be suitable for use in treating symptoms related to an enlarged prostate gland, a condition known as Benign Prostatic Hyperplasia (BPH). BPH is a common condition in which the prostate becomes enlarged with aging. The prostate is a gland that is part of the male reproductive system. The prostate gland includes two lobes that are enclosed by an outer layer of tissue and is located below the bladder and surrounding the urethra, the canal through which urine passes out of the body. Prostate growth can occur in different types of tissue and can affect men differently. As a result of these differences, treatment varies in each case. No cure for BPH exists and once the prostate begins to enlarge, it often continues, unless medical treatment is initiated.

Patients who develop symptoms associated with BPH generally need some form of treatment. When the prostate gland is mildly enlarged, research studies indicate that early treatment may not be needed because the symptoms clear up without treatment in as many as one-third of cases. Instead of immediate treatment, regular checkups are recommended. Only if the condition presents a health risk or the symptoms result in major discomfort or inconvenience to the patient is treatment generally recommended. Current forms of treatment include drug treatment, minimally-invasive therapy, and surgical treatment. Drug treatment is not effective in all cases and a number of procedures have been developed to relieve BPH symptoms that are less invasive than conventional surgery.

While drug treatments and minimally-invasive procedures have proven helpful for some patients, many doctors still recommend surgical removal of the enlarged part of the prostate as the most appropriate long-term solution for patients with BPH. For the majority of cases that require surgery, a procedure known as Transurethral Resection of the Prostate (TURP) is used to relieve BPH symptoms. In this procedure, the medical practitioner inserts an instrument called a resectoscope into and through the urethra to remove the obstructing tissue. The resectoscope also provides irrigating fluids that carry away the removed tissue to the bladder.

More recently, laser-based surgical procedures employing, for example, side-firing optical fibers and high-power lasers have been used to remove obstructing prostate tissue. In these procedures, a medical practitioner passes the optical fiber through the urethra using a cystoscope, a specialized endoscope with a small camera on the end, and then delivers multiple bursts of laser energy to destroy some of the enlarged prostate tissue and to shrink the size of the prostate. Patients who undergo laser surgery usually do not require overnight hospitalization and in most cases the catheter is removed the same day or the morning following the procedure. Generally, less bleeding occurs with laser surgery and recovery times tend to be shorter than those of traditional procedures such as TURP surgery.

A common laser-based surgical procedure is Holmium Laser Enucleation of the Prostate (HoLEP). In this procedure, a holmium:YAG (Ho:YAG) laser is used to remove obstructive prostate tissue. The Ho:YAG surgical laser is a solid-state, pulsed laser that emits light at a wavelength of approximately 2100 nm. This wavelength of light is particularly useful for tissue ablation as it is strongly absorbed by water. An advantage of Ho:YAG lasers is that they can be used for both tissue cutting and for coagulation. Another common laser surgery procedure is Holmium Laser Ablation of the Prostate (HoLAP), where a Ho:YAG laser is used to vaporize obstructive prostate tissue. The decision whether to use HoLAP or HoLEP is based primarily on the size of the prostate. For example, ablation may be preferred when the prostate is smaller than 60 cc (cubic centimeters). Laser-based surgical procedures, such as HoLAP and HoLEP, are becoming more preferable because they produce similar results to those obtained from TURP surgery while having fewer complications and requiring shorter hospital stay, shorter catheterization time, and shorter recovery time.

An optical fiber system as described herein can be used to transmit laser energy from a laser source to a target treatment area within a patient's body. The optical fiber system can include a laser source and an optical fiber. One end of the optical fiber can be coupled to the laser source while the other end of the optical fiber, the distal end portion (e.g., the end with a side-firing or end-firing portion), can be inserted into the patient's body to provide laser treatment. The distal end portion can include a capillary. In some instances, a metal cap or a low-profile cover can be placed over the capillary. In one embodiment, an angled or beveled end surface of the optical fiber core disposed within the capillary can redirect laser energy for side-firing or laterally-firing transmission of laser energy to the area of treatment. The angled end surface of the core can include, for example, a multilayer dielectric coating. The multilayer dielectric coating can be configured to reflect a portion of the optical beam (e.g., laser beam) from the optical fiber that impinges on the end surface of the core at a less glancing angle and would not otherwise be totally internally reflected. The multilayer dielectric coating can also be disposed on an outer surface of the distal end portion of the optical fiber core having at least portion of the cladding stripped. Examples of optical fibers that can have at least portion of the cladding stripped include polymer-clad optical fibers and glass-clad optical fibers. The multilayer dielectric coating and the angled surface can be collectively configured to redirect laser energy in a lateral or side-fired direction.

In another embodiment, a substantially perpendicular end surface of the optical fiber core disposed within the capillary can direct laser energy for end-firing transmission of laser energy to the area of treatment. The outer surface of the distal end portion of the optical fiber core can include, for example, a multilayer dielectric coating. The multilayer dielectric coating and the substantially perpendicular surface can be collectively configured to direct laser energy in a parallel or end-fired direction.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., medical practitioner, medical practitioner, nurse, technician, etc.) who would insert the medical device into the patient, with the tip-end (i.e., distal end) of the device inserted inside a patient's body. Thus, for example, the optical fiber end inserted inside a patient's body would be the distal end of the optical fiber, while the optical fiber end outside a patient's body would be the proximal end of the optical fiber.

FIGS. 1A-1B are schematic representations of an optical fiber side-firing and end-firing system according to an embodiment. As shown in FIG. 1A, an optical fiber side-firing system 10 can include a laser source 11, an optical coupler 12, an optical fiber 14, and an optical-fiber distal end portion 16. The optical fiber side-firing system 10 also includes a suitable catheter or endoscope 15 for inserting the optical-fiber distal end portion 16 into a patient's body. The laser source 11 can include at least one laser that can be used for generating laser energy for surgical procedures. The laser source 11 can include a Ho:YAG laser, for example. The laser source 11 can include at least one of a neodymium-doped:YAG (Nd:YAG) laser, a semiconductor laser diode, or a potassium-titanyl phosphate crystal (KTP) laser, for other examples. In some embodiments, more than one laser can be included in the laser source 11 and more than one laser can be used during a surgical procedure. The laser source 11 can also have a processor that provides timing, wavelength, and/or power control of the laser. For example, the laser source 11 can include mechanisms for laser selection, filtering, temperature compensation, and/or Q-switching operations.

The optical fiber 14 can be coupled to the laser source 11 through the optical coupler 12. The optical coupler 12 can be an SMA connector, for example. The proximal end of the optical fiber 14 can be configured to receive laser energy from the laser source 11 and the distal end of the optical fiber 14 can be configured to output the laser energy through the optical-fiber distal end portion 16. The optical fiber 14 can include, for example, a core, one or more cladding layers about the core, a buffer layer about the cladding, and a jacket. The core can be made of a suitable material for the transmission of laser energy from the laser source 11. In some embodiments, when surgical procedures use wavelengths ranging from about 500 nm to about 2100 nm, the core can be made of silica with a low hydroxyl ($OH^-$) ion residual concentration. An example of using low hydroxyl (low-OH) fibers in medical devices is described in U.S. Pat. No. 7,169,140 to Kume, the disclosure of which is incorporated herein by reference in its entirety. The core can be single or multi-mode and can have a step or graded index profile. The cladding can be a single or a double cladding that can be made of a hard polymer or silica. The buffer can be made of a hard polymer such as Tefzel®, for example. When the optical fiber includes a jacket, the jacket can be made of Tefzel®, for example, or can be made of other polymers.

The endoscope 15 can define one or more lumens. In some embodiments, the endoscope 15 includes a single lumen that can receive therethrough various components such as the optical fiber 14. The endoscope 15 has a proximal end configured to receive the optical-fiber distal end portion 16 and a distal end configured to be inserted into a patient's body for positioning the optical-fiber distal end portion 16 in an appropriate location for a laser-based surgical procedure. For example, to relieve symptoms associated with BPH, the endoscope 15 can be used to place the optical-fiber distal end portion 16 at or near the enlarged portion of the prostate gland. The endoscope 15 includes an elongate portion that can be flexible to allow the elongate portion to be maneuvered within the body. The endoscope 15 can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et, al., the disclosure of which is incorporated herein by reference in its entirety. In some embodiments, a fluid channel (not shown) is defined by the endoscope 15 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope 15, for example, and coupled to an optical fiber that can be disposed within a lumen of the endoscope 15. Such an embodiment allows a medical practitioner to view the interior of a patient's body through the eyepiece.

The optical-fiber distal end portion 16 can include one or more members, elements, or components that can individually or collectively operate to transmit laser energy in a lateral direction offset from a longitudinal axis or centerline of the distal end of the optical fiber core. In some embodiments, the optical-fiber distal end portion 16 can have a protective metal or ceramic cap or cover. In other embodiments, the optical-fiber distal end portion 16 can have a protective low-profile coating or a low-profile slideable sleeve or tubing than can be retracted to expose the optical-fiber distal end portion 16 to a treatment area during a surgical procedure.

In FIG. 1B, an optical fiber end-firing system 13 is shown that can include the laser source 11, the optical coupler 12, the optical fiber 14, and an optical-fiber distal end portion 17. The optical fiber end-firing system 13 can also include the catheter or endoscope 15 for inserting the optical-fiber distal end portion 17 into a patient's body. The optical-fiber distal end portion 17 can include one or more members, elements, or components that can individually or collectively operate to transmit laser energy in a direction substantially parallel to the longitudinal axis or centerline of the distal end of the optical fiber core. In some embodiments, the optical-fiber distal end portion 17 can have a protective metal or ceramic cap or cover. In other embodiments, the optical-fiber distal end portion 17 can have a protective low-profile coating.

FIGS. 2A-2B are cross-sectional views of the optical-fiber distal end portion 16 and 17, respectively, according to embodiments. As shown in FIG. 2A, the optical-fiber distal end portion 16 can include an inner portion 20 and surrounded by an outer portion 22. The outer portion 22 can include a high-profile member such as, for example, a metal or ceramic cover or cap. The cover or cap is generally made of surgical grade stainless steel or other materials with like properties. In some instances, it can be desirable to have the cap made of a ceramic material (e.g., alumina) since certain ceramics can offer stable characteristics at high-temperatures and/or have a high reflectance value at the laser operating wavelength. The outer portion 22 can provide protection to the optical-fiber distal end portion 16. In some embodiments, the outer portion 22 can include a low-profile coating or a low-profile sleeve.

The outer portion 22 can include a window or transmissive portion 18 through which laterally-redirected or side-fired laser energy can be transmitted for surgical treatment. For example, when the outer portion 22 is made of an opaque material, a window can be defined after removing at least a portion of the opaque material. In another example, when the outer portion 22 is made of an optically-transmissive material, laser energy can be transmitted or sent through the outer portion 22. In some embodiments, the optically-transmissive material can be treated thermally, optically, mechanically, and/or chemically to improve its structural and/or optical characteristics such that laser energy can be delivered more effectively to the target area. For example, the optically-transmissive material can be thermally treated during manufacturing using a $CO_2$ laser.

The inner portion 20 can include one or more members, components, and/or devices to redirect laser energy. For example, the inner portion 20 can include a capillary or capillary tube. The capillary can be made of, for example, at least one of silica, sapphire, and/or other like materials. In one embodiment, the inner portion 20 can include a distal end portion of the core of the optical fiber 14 disposed within a capillary. As described below in more detail, the inner portion 20 can also include reflecting coatings, members and/or mirrors that can be used to redirect laser energy to provide side-firing operations.

In FIG. 2B, the optical-fiber distal end portion 17 can include an inner portion 21 and surrounded by an outer portion 23. The outer portion 23 can be substantially similar to the outer portion 22 described in FIG. 2A. The outer portion 23 can include, however, a window or transmissive portion 19 through which end-fired laser energy can be transmitted for surgical treatment. The inner portion 21 can include one or more members, components, and/or devices to direct laser energy in a direction substantially parallel to the longitudinal axis or centerline of the distal end of the optical fiber core. For example, the inner portion 21 can include a capillary or capillary tube. The capillary can be made of, for example, at least one of silica, sapphire, and/or other like materials. In one embodiment, the inner portion 21 can include a distal end portion of the core of the optical fiber 14 disposed within a capillary. As described below in more detail, the inner portion 21 can also include reflecting members and/or mirrors that can be used to direct laser energy to provide end-firing operations.

FIGS. 3A-3B are side views illustrating laser energy leakage that may occur in side-firing and end-firing optical fibers. As shown in FIG. 3A, an optical fiber 114 can include, for example, a core 134, one or more cladding layers 132 about the core 134, a buffer layer 130 about the cladding 132, and a jacket (not shown in FIGS. 3A-3B). The core 134 can be made of a suitable material, for example, silica glass ($SiO_2$), for the transmission of laser energy for laser-based surgical procedures. The cladding 132 can be made of a material, for example, a hard polymer or silica, which has a refractive index that is slightly lower than that of the core 134. The refractive index of a silica core and/or a silica cladding can be controlled by adjusting the concentrations of doping materials (e.g. titanium, germanium, or boron) added to the silica. An appropriate difference in refractive index between the core 134 and the cladding 132 results in confined propagation or transmission of laser energy within the core 134. The buffer layer 130 can be made of a hard polymer and is generally used to protect the core 134 and the cladding layer 132 from, for example, moisture and/or other types of environmental damage.

As shown in FIG. 3A, the distal end portion of the optical fiber 114 can have a portion of the cladding layer 132 and a portion of the buffer layer 130 removed. The portion of the core 134 that is exposed by the removal of the cladding layer 132 and the buffer layer 130 includes a core end surface 138 that is angled relative to a longitudinal axis or centerline 119 of a distal end portion of the core 134. In some instances, the distal end of the cladding layer 132 can extend to the distal end of the core 134 (e.g., the polished end). A portion A of the laser energy transmitted through the core 134 can be redirected by the core-end angled surface 138 in a direction that is offset the longitudinal axis or centerline. Removal of the cladding layer 132, however, reduces the ability of the core 134 to provide laser energy confinement and another portion B of the laser energy transmitted through the core 134 can therefore leak out through the outer surface of the exposed portion of the core 134. Moreover, another portion C of the laser energy transmitted through the core 134 can leak out through the core-end angled surface 138 when the angle of incidence of the laser energy onto the core-end angled surface 138 does not produce total internal reflection (TIR) in the offset or side-firing direction.

FIG. 3B shows a core 135 having a distal end or terminating surface 139 that is substantially perpendicular relative to the longitudinal axis or centerline 136 of the distal end portion of the core 135. In some instances, the distal end of the cladding layer 132 can extend to the distal end of the core 135 (e.g., the polished end). A portion D of the laser energy transmitted through the core 135 can be transmitted through the core-end perpendicular surface 139 in a direction that is substantially parallel to the longitudinal axis 136. As described above, a portion E of the laser energy transmitted through the core 135 can also leak out through the outer surface of the exposed portion of the core 135. The end-leakage and side-leakage of laser energy described in FIGS. 3A and 3B can produce overheating and/or damage to the optical fiber 114, to a capillary (not shown) and/or to a protective layer or cap (not shown), for example.

FIGS. 4A-4B are cross-sectional views of a side-firing optical fiber 214 with different capillaries, according to embodiments. As shown in FIG. 4A, the side-firing optical fiber 214 has a buffer layer 230, a cladding layer 232, and an optical-fiber-core end portion 234. Also shown is a capillary 236 within which the optical-fiber-core end portion 234 is disposed. The capillary 236 can be made of an optically-transmissive material such that a side-fired laser energy 244 can be transmitted through the capillary 236.

In some embodiments, a proximal end portion of the capillary 236 can be coupled to a distal end portion of the cladding layer 232 and/or a distal end portion of the buffer layer 230 of the side-firing optical fiber 214 through a fusion process that produces an interface or fusion region 231. For example, a $CO_2$ laser can be used during manufacturing to perform the fusion operation. In some embodiments, to minimize laser energy reflections that can occur between the side-firing optical fiber 214 and the capillary 236, the refractive indices of the buffer layer 230 and/or the cladding layer 232 of the side-firing optical fiber 214 can be substantially matched to the refractive index of the capillary 236. Reducing or minimizing the formation of bubbles, air gaps, and/or defects at the fusion region 231 during the fusion process can also minimize interface reflections. The $OH^-$ ion concentration of the cladding layer 232 and/or the buffer layer 230 can also be controlled to match that of the capillary 236. Matching refractive indices can improve the mechanical and/or optical integrity of the fusion region 231 by minimizing thermal behavior differences between the distal end portion of the optical fiber 214 and the capillary 236. Moreover, matching the refractive index of the capillary 236 to that of the cladding layer 232 can improve confinement of laser energy to within the optical-fiber-core end portion 234 where the cladding layer 232 has been removed.

As shown in FIG. 4A, the optical-fiber-core end portion 234 can include a core-end angled surface 238 that is angled or beveled relative to a longitudinal axis or centerline 239 of the optical-fiber-core end portion 234. The core-end angled surface 238 can be polished such that the appropriate angle is achieved. The core-end angled surface 238 can be configured such that the angled surface produces reflection of laser energy that is transmitted through the optical fiber end portion 234 to laterally redirect or side-fire the laser energy F.

The angle of the core-end angled surface 238 can be determined based on at least one of several parameters. For example, the angle can be configured based on the wavelength of the laser energy F, the exit or output location for the side-fired laser energy F, and/or the optical properties of the optical-fiber-core end portion 234 and/or the capillary 236. Moreover, the optical properties of a region 241 located between the core-end angled surface 238 and the inner portion of the distal end of the capillary 236 can also be used in determining an appropriate angle for the core-end angled surface 238. By determining an appropriate angle for the core-end angled surface 238, the side-fired laser energy 244 can be transmitted in a lateral direction that is appropriate for laser-based surgical procedures.

In some instances, some of the laser energy transmitted through the optical-fiber-core end portion 234 is not laterally reflected at the core-end angled surface 238 and instead it is transmitted to the region 241 and then through the optically-transmissive distal end of the capillary 236. This laser energy leakage is thus transmitted in a direction that is substantially parallel to longitudinal axis or centerline 239 of the distal end portion of the side-firing optical fiber 14 and not in a side-fired or laterally-redirected direction. To minimize the amount of laser energy that is leaked in this manner, the core-end angled surface 238 can also include a reflective coating that operates collectively with the angle of incidence of the laser energy to increase the efficiency with which the laser energy transmitted through the optical-fiber-core end portion 234 is laterally redirected for side-firing operations.

As shown in FIG. 4A, the core-end angled surface 238 can include a multilayer dielectric coating 240 to reduce or limit leakage of laser energy through the core-end angled surface 238. The multilayer dielectric coating 240 can be made of multiple dielectric layers that collectively and efficiently operate to reflect laser energy. A dielectric layer can be made of alternating layers of $SiO_2$ (silica) and $TiO_2$ (titanium dioxide or titania), for example. The multilayer dielectric coating 240 can include alternating layers of two or more materials each with a different dielectric constant. In some embodiments, the multilayer dielectric coating 240 can be configured to operate as a ¼ wavelength mirror in which sets of two alternating layers are used and each layer has an optical thickness that is ¼ the wavelength of the laser energy. The multilayer dielectric material 240 can be deposited on the core-end angled surface 238 by using any of multiple deposition techniques, such as electron beam or ion beam deposition, for example.

The multilayer dielectric coating 240 can be used to improve the reflection efficiency of the core-end angled surface 238 over a wider range of angles associated with the laser beam propagation through the optical fiber. The high reflectivity and low optical absorption of multilayer dielectric coatings can reduce the device operating temperature and/or reduce the amount of cooling that may be used to operate the device at a safe temperature.

In another embodiment, as shown in FIG. 4B, a capillary 286 can be made of an opaque material. In this instance, a window or transmissive portion 282 can be defined in a region of the capillary 286 that is offset to the longitudinal axis or centerline 279 of the optical-fiber-core end portion 274 for transmission of the side-fired laser energy G. The capillary 286 can be coupled to a distal end portion of the cladding layer 272 and/or a distal end portion of a buffer layer 270 of the side-firing optical fiber 254 through a fusion process that produces an interface or fusion region 275. In this instance, the mechanical and/or thermal properties of the capillary 286, the buffer layer 270 and/or the cladding layer 272 can be substantially matched to provide better overall performance when using the device.

FIG. 5 is a cross-sectional view of a distal end portion of a side-firing optical fiber 314 with a capillary 336, according to another embodiment. As shown in FIG. 5, the side-firing optical fiber 314 has a buffer layer 330, a cladding layer 332, and an optical-fiber-core end portion 334. Also shown is the capillary 336 within which the optical-fiber-core end portion 334. The capillary 336 can be made of an optically-transmissive material such that a side-fired laser energy H can be transmitted through the capillary 336.

The optical-fiber-core end portion 334 can include a core-end angled surface 338 that is angled or beveled relative to a longitudinal axis or centerline 339 of the optical-fiber-core end portion 334. The core-end angled surface 338 can include a multilayer dielectric coating 340 to limit or reduce the amount of laser energy leakage that can occur through the core-end angled surface 338. Moreover, a portion of the outer surface of the optical-fiber-core end portion 334 can also include the multilayer dielectric coating 340 to reduce or limit the amount of laser energy leakage that can occur through the outer surface of the optical-fiber-core end portion 334 in a direction opposite to the side-fired direction. The outer surface of the optical-fiber-core end portion 334 can be offset from the longitudinal axis 339. In one embodiment, the multilayer dielectric coating 340 disposed on the core-end angled surface 338 and on the portion of the outer surface of the optical-fiber-core end portion 334 can be substantially similar coatings. In another embodiment, the multilayer dielectric coating 340 disposed on the core-end angled surface 338 and on the portion of the outer surface of the optical-fiber-core end portion 334 can be different coatings. The core-end angled surface 338 and the multilayer dielectric coating 340 can be collectively configured to reduce laser energy leakage and increase the amount of laser energy H that is side-fired or laterally-fired during laser-based surgical procedures.

Figure 6A:
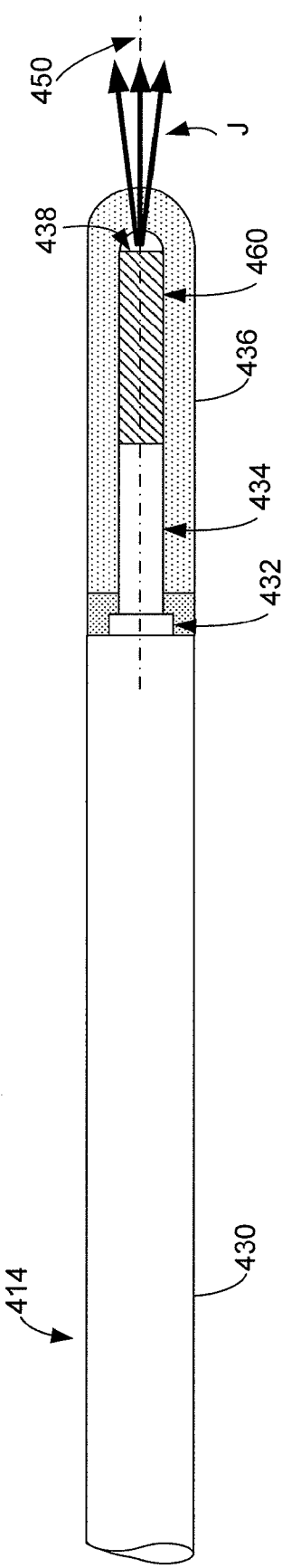
FIG. 6A is a cross-sectional view of an end-firing optical fiber with a capillary, according to an embodiment.
Figure 6B:
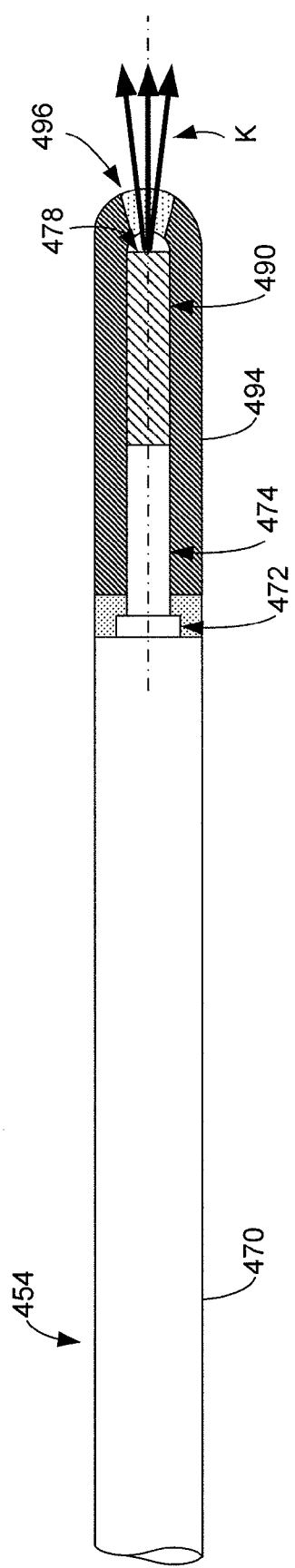
FIG. 6B is a cross-sectional view of an end-firing optical fiber with a capillary, according to another embodiment.

FIG. 6A is a cross-sectional view of an end-firing optical fiber 414 with a capillary 436, according to embodiments. As shown in FIG. 6A, the end-firing optical fiber 414 has a buffer layer 430, a cladding layer 432, and an optical-fiber-core end portion 434. Also shown is the capillary 436 within which the optical-fiber-core end portion 434 is disposed. The capillary 436 can be made of an optically-transmissive material such that a side-fired laser energy J can be transmitted through the distal end of the capillary 436. In another embodiment, as shown in FIG. 6B, an end-firing optical fiber 454 has a capillary 494 that can be made of an opaque material. In this instance, a distal end of the capillary 494 defines a window or transmissive portion 496 through which the end-fired laser energy K can be transmitted.

The optical-fiber-core end portion 434 can include a core end surface 438 that is substantially perpendicular relative to a longitudinal axis or centerline 450 of a the optical-fiber-core end portion 434. A portion of the outer surface of the optical-fiber-core end portion 434 can include the multilayer dielectric coating 460 to reduce or limit the amount of laser energy leakage that can otherwise occur through the outer surface of the optical-fiber-core end portion 434. The core end surface 438 and the multilayer dielectric coating 460 can be collectively configured to reduce laser energy leakage and increase the amount of laser energy 444 that is end-fired during laser-based surgical procedures.

FIG. 7A is a side view of a coated core-end surface according to an embodiment. The core-end surface 538 can be non-perpendicular to a longitudinal axis 539. A multilayer dielectric coating 540 can be disposed on or deposited on the core-end surface 538 based on various deposition techniques. The core-end surface 538 and the multilayer dielectric coating 540 can collectively redirect laser energy in direction substantially parallel to an exit direction 535. In the example shown, the multilayer dielectric coating 540 can coat or cover the entire core-end surface 538. In another example (not shown), the multilayer dielectric coating 540 can coat or cover a portion of the core-end surface 538 that is less than the entire surface. In FIG. 7B, an end view taken along line A-A of FIG. 7A shows an uncoated outer surface of the opticalfiber-core end portion 534. In this embodiment, the higher reflectivity over a wider range of optical wavelengths of the multilayer dielectric coating 540 can be used to reduce or limit the amount of laser energy leakage that can occur through the core-end surface 538 during side-firing operations. Moreover, this approach may also reduce overheating of the device during laser-based surgical procedures.

In FIG. 8A, a side view of a coated optical-fiber-core end portion 634 and a coated core-end surface is shown, according to an embodiment. The core-end surface 638 can be non-perpendicular to a longitudinal axis 639. A multilayer dielectric coating 640 that can be disposed on or deposited on the core-end surface 638 based on various deposition techniques. In the example shown, the multilayer dielectric coating 640 can coat or cover the entire core-end surface 638. In another example (not shown), the multilayer dielectric coating 640 can coat or cover a portion of the core-end surface 638 that is less than the entire surface. A portion of the outer surface of the optical-fiber-core end portion 634 can also include the multilayer dielectric coating 640. The outer surface of the optical-fiber-core end portion 634 can be offset from the longitudinal axis 639. In the example shown, approximately the lower half of the outer surface of the distal end portion of the optical-fiber-core end portion 634 can include the multilayer dielectric coating 640. The lower half of the outer surface may be opposite to the exit direction 635 of the optical-fiber-core end portion 634 through which the side-fired laser energy is transmitted. In FIG. 8B, an end view taken along line B-B of FIG. 8A shows the multilayer dielectric coating 640 disposed on the lower half of the outer surface of the optical-fiber-core end portion 634.

In another embodiment, as shown in FIG. 9A, a core-end surface 738 can be non-perpendicular to a longitudinal axis 739. A multilayer dielectric coating 740 can be disposed on or deposited the core-end surface 738 based on various deposition techniques such as electron beam or ion beam deposition. In the example shown, the multilayer dielectric coating 740 can coat or cover the entire core-end surface 738. In another example (not shown), the multilayer dielectric coating 740 can coat or cover a portion of the core-end surface 738 that is less than the entire surface. A portion of an outer surface of the optical-fiber-core end portion 734 can also include the multilayer dielectric coating 740. The outer surface of the optical-fiber-core end portion 734 can be offset from the longitudinal axis 739. In the example shown, a lower half portion of the outer surface of the distal end portion of the optical-fiber-core end portion 734 can include the multilayer dielectric coating 740. The lower half of the outer surface may be opposite to the exit direction 735 of the optical-fiber-core end portion 734 through which the side-fired laser energy is transmitted. In FIG. 9B, an end view taken along line C-C of FIG. 9A shows the multilayer dielectric coating 740 disposed on the lower half portion of the outer surface of the optical-fiber-core end portion 734.

In FIG. 10A, a side view of a coated optical-fiber-core end portion and a coated core-end surface is shown, according to an embodiment. The core-end surface 838 can be non-perpendicular to a longitudinal axis 839. A multilayer dielectric coating 840 can be disposed on or deposited on the core-end surface 838 based on various deposition techniques. In the example shown, the multilayer dielectric coating 840 can coat or cover the entire core-end surface 838. In another example (not shown), the multilayer dielectric coating 840 can coat or cover a portion of the core-end surface 838 that is less than the entire surface. A portion of the outer surface of the optical-fiber-core end portion 834 can also include the multilayer dielectric coating 840. The outer surface of the optical-fiber-core end portion 834 can be offset from the longitudinal axis 839. In the example shown, the lower half and a portion of the upper half of the outer surface of the distal end portion of the optical-fiber-core end portion 834 can include the multilayer dielectric coating 840. The lower half of the outer surface may be opposite to the exit direction 835 of the optical-fiber-core end portion 834 through which the side-fired laser energy is transmitted. FIG. 10B shows an end view taken along line D-D of FIG. 10A where the multilayer dielectric coating 840 is disposed on the lower half and the upper half portion of the outer surface of the optical-fiber-core end portion 834.

In the embodiments described in FIGS. 8A, 8B, 9A, 9B, 10A, and 10B, the core-end surface and/or the multilayer dielectric coating can collectively redirect laser energy in direction substantially parallel to an exit direction. The multilayer dielectric coating disposed on the core-end surface and on a portion of the outer surface of the optical-fiber-core end portion can be used to reduce or limit the amount of laser energy leakage that can occur such that the amount of side-fired laser energy delivered for patient treatment is increased. Moreover, this approach can also produce reduced overheating of the device during side-fired laser-based surgical procedures.

FIG. 1A shows a side view of a coated optical-fiber-core end portion and a coated core-end surface, according to an embodiment. The core-end surface 938 can be non-perpendicular to a longitudinal axis 939. A first multilayer dielectric coating 940 can be disposed on or deposited on the core-end surface 938 based on various deposition techniques. In the example shown, the first multilayer dielectric coating 940 can coat or cover the entire core-end surface 938. In another example (not shown), the first multilayer dielectric coating 940 can coat or cover a portion of the core-end surface 938 that is less than the entire surface.

A second multilayer dielectric coating 942 can be disposed on a portion of the outer surface of the optical-fiber-core end portion 934 using various deposition techniques. The outer surface of the optical-fiber-core end portion 934 can be offset from the longitudinal axis 939. In the example shown, approximately the lower half of the outer surface of the distal end portion of the optical-fiber-core end portion 934 can include the second multilayer dielectric coating 942. In this example, the distal end of the second multilayer dielectric coating 942 can be proximate to the core-end surface 938. The first multilayer dielectric coating 940 and the second multilayer dielectric coating 942 can be different and can be deposited using separate and/or different deposition techniques. The first multilayer dielectric coating 940 and the second multilayer dielectric coating 942 can include different number of layers, different number of materials, and/or different layer thicknesses, for example. FIG. 11B shows an end view taken along line E-E of FIG. 11A where the second multilayer dielectric coating 942 is disposed on a portion of the lower half of the outer surface of the optical-fiber-core end portion 934.

In another embodiment, shown in FIG. 12A, a first multilayer dielectric coating 1040 can be disposed on a core-end surface 1038 that is non-perpendicular to a longitudinal axis 1039. A second multilayer dielectric coating 1042 can be disposed on a portion of an outer surface of an optical-fiber-core end portion 1034 that is offset from the longitudinal axis 1039. In the example shown, the second multilayer dielectric coating 1042 can cover a portion of the outer surface of the optical-fiber-core end portion 1034 that is not immediately proximate to the core-end surface 1038. In this regard, a distal end of the second multilayer dielectric coating 1042 is offset from the core-end surface 1038. As with the embodiment shown in FIGS. 1A and 1B, the first multilayer dielectric coating 1040 and the second multilayer dielectric coating 1042 can be different and can be deposited using separate and/or different deposition techniques. FIG. 12B is an end view taken along line F-F of FIG. 12A. As shown in FIG. 12B, the second multilayer dielectric coating 1042 is disposed on a portion of the lower half of the outer surface of the optical-fiber-core end portion 1034.

FIG. 13A shows a side view of a coated optical-fiber-core end portion according to an embodiment. A multilayer dielectric coating 1140 can be disposed on a portion of the outer surface of the optical-fiber-core end portion 1134. The outer surface of the optical-fiber-core end portion 1134 is offset from a longitudinal axis 1139. In the example shown, the multilayer dielectric coating 1140 can be disposed on approximately the lower half of the outer surface of the distal end portion of the optical-fiber-core end portion 1134. In this example, the multilayer dielectric coating 1140 can cover the outer surface proximate to the core-end surface 1138. FIG. 13B is an end view taken along line G-G of FIG. 13A. As shown in FIG. 13B, the multilayer dielectric coating 1140 is disposed on approximately the lower half of the outer surface of the optical-fiber-core end portion 1134.

In another embodiment, shown in FIG. 14A, a multilayer dielectric coating 1240 can be disposed on a portion of an outer surface of an optical-fiber-core end portion 1234. The outer surface of the optical-fiber-core end portion 1234 is offset from a longitudinal axis 1239. In the example shown, the multilayer dielectric coating 1240 can cover a portion of the outer surface of the optical-fiber-core end portion 1034 that does not terminate at a core-end surface 1238. In this regard, a distal end of the multilayer dielectric coating 1240 is offset from the core-end surface 1238. FIG. 14B shows an end view taken along line H-H of FIG. 14A. As shown in FIG. 14B, the multilayer dielectric coating 1240 is disposed on approximately the lower half of the outer surface of the optical-fiber-core end portion 1234.

In the embodiments described in FIGS. 11A, 11B, 12A, 12B, 13A, 13B, 14A, and 14B, a multilayer dielectric coating disposed on the core-end surface and/or a multilayer dielectric coating disposed on a portion of the optical-fiber-core end portion can be used to reduce or limit the amount of laser energy leakage that can occur such that the amount of side-fired laser energy delivered for patient treatment is increased. Moreover, this approach can also produce reduced overheating of the device during side-fired laser-based surgical procedures. While the examples in these figures have shown a multilayer dielectric coating on approximately a lower half of the outer surface of the optical-fiber-core end portion, the invention need not be so limited. Other examples (not shown) can include those in which the multilayer dielectric coating covers a lower half portion and more than the lower half of the outer surface of the optical-fiber-core end portion.

Figure 15B:
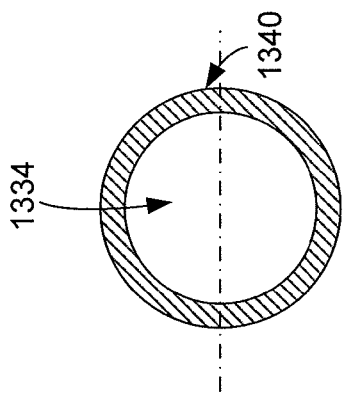
FIG. 15B is an end view taken along line I-I of FIG. 15A.
Figure 16B:
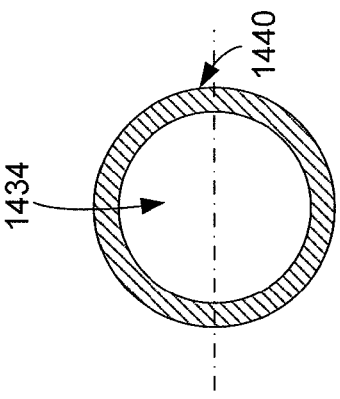
FIG. 16B is an end view taken along line J-J of FIG. 16A.
Figure 15A:
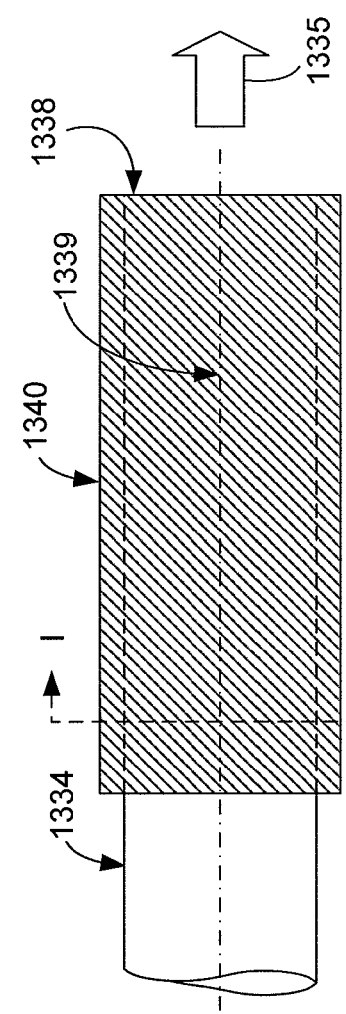
FIG. 15A is a side view of a coated core end portion and a core-end surface, according to an embodiment.

In FIG. 15A, a side view of a coated optical-fiber-core end portion is shown according to an embodiment. A multilayer dielectric coating 1340 can be disposed on a distal end portion of the outer surface of an optical-fiber-core end portion 1334. In this example, the multilayer dielectric coating 1340 can cover the outer surface proximate to the core end surface 1338. The core end surface 1338 is substantially perpendicular to a longitudinal axis or centerline 1339 of the distal end of the optical-fiber-core end portion 1334. FIG. 15B is an end view taken along line I-I of FIG. 15A. As shown in FIG. 15B, the multilayer dielectric coating 1340 is disposed on the outer surface of the optical-fiber-core end portion 1334.

Figure 16A:
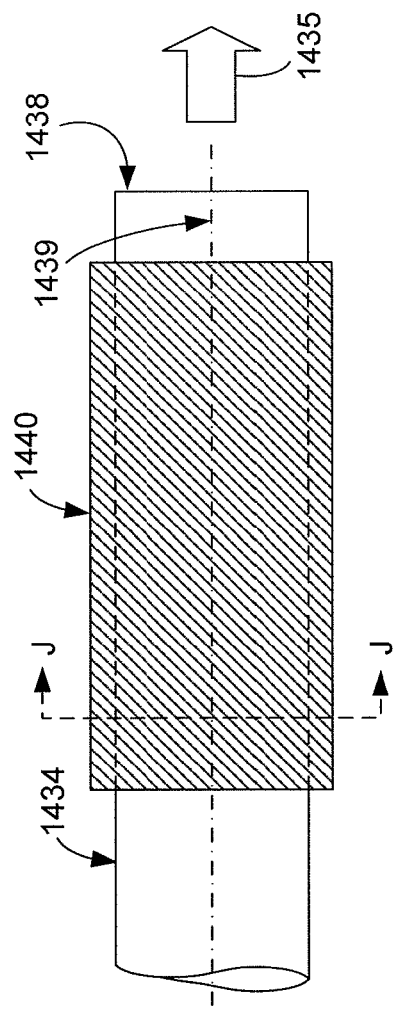
FIG. 16A is a side view of a coated core end portion and a core-end surface, according to another embodiment.

In another embodiment, shown in FIG. 16A, a multilayer dielectric coating 1440 can be disposed on a portion of an outer surface of an optical-fiber-core end portion 1434. In the example shown, the multilayer dielectric coating 1440 can cover a portion of the outer surface of the optical-fiber-core end portion 1434 that does not terminate at the core end surface 1438. In this regard, a distal end of the multilayer dielectric coating 1440 is offset from the core end surface 1438. FIG. 14B is an end view taken along line J-J of FIG. 14A. As shown in FIG. 14B, the multilayer dielectric coating 1240 is disposed on the outer surface of the optical-fiber-core end portion 1234.

In the embodiments described in FIGS. 15A, 15B, 16A, and 16B, a multilayer dielectric coating disposed on a portion of the optical-fiber-core end portion can be used to reduce or limit the amount of laser energy leakage that can occur such that the amount of end-fired laser energy delivered for patient treatment is increased. Moreover, this approach can also result in reduced overheating of the device during end-fired laser-based surgical procedures.

Figure 17:
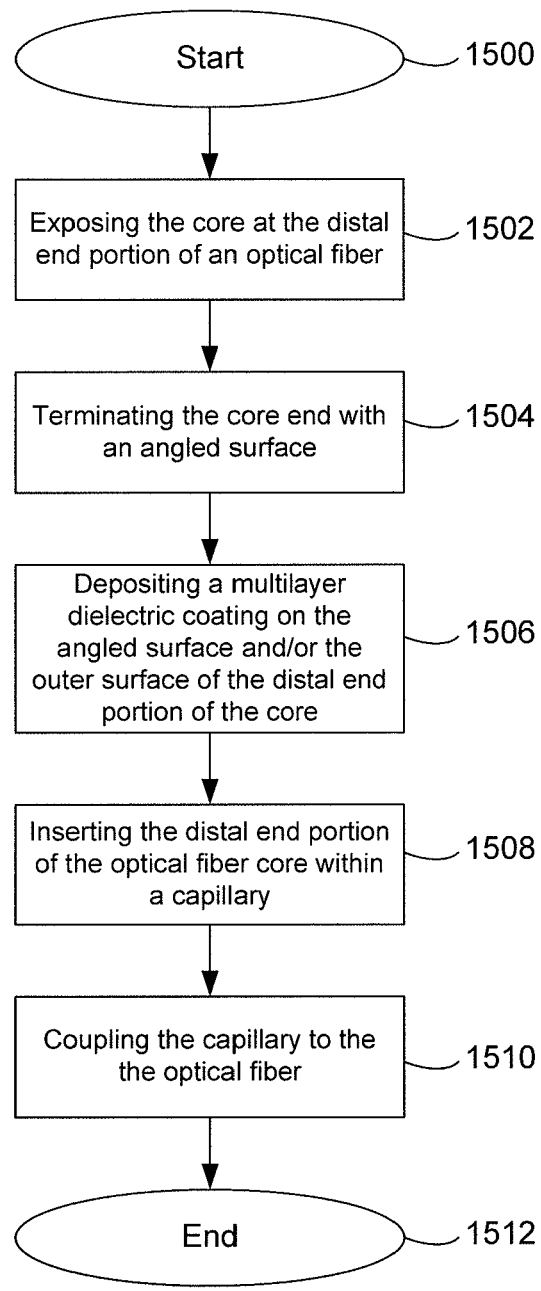
FIGS. 17-19 are flow charts illustrating a method according to an embodiment.

FIG. 17 is a flow chart illustrating a method for manufacturing a side-firing optical fiber, according to an embodiment. At 1502, after start 1500, a distal end portion of an optical fiber core can be exposed by removing a distal end portion of an optical fiber cladding and an optical fiber buffer from an optical fiber. At 1504, the distal end portion of the optical fiber core can be terminated with an angled or beveled end surface. The angled end surface can be produced by polishing the distal end surface of the optical fiber core. At 1506, a multilayer dielectric coating can be deposited on the angled end surface and/or on the outer surface of the distal end portion of the optical fiber core to reduce the amount of laser energy leakage that can occur in side-fired operations. In this regard, more than one multilayer dielectric coating can be used.

At 1508, the exposed distal end portion of the optical fiber core can be disposed within an inner portion of a capillary. Optionally, the remaining volume within the inner portion of the capillary after the disposing of the optical fiber core can be filled with a gas, a liquid, and/or a solid to improve the reflection at the angled end surface. In other words, the use of a gas, liquid, and/or solid can have an index of refraction different than air. This index of refraction can alter the amount of laser energy that is reflected at the angled surface. At 1510, a proximal end portion of the capillary can be coupled to the distal end portion of the optical fiber. In one example, the proximal end portion of the capillary and the distal end portion of the optical fiber can be fused together, which may result in an interface or fusion region. Optionally, a cover, such as a metal cap or a low-profile cover, for example, can be deposited on the outer surface of the capillary and/or on the distal end portion of the buffer layer. After 1510, the method can proceed to end 1512.

Figure 18:
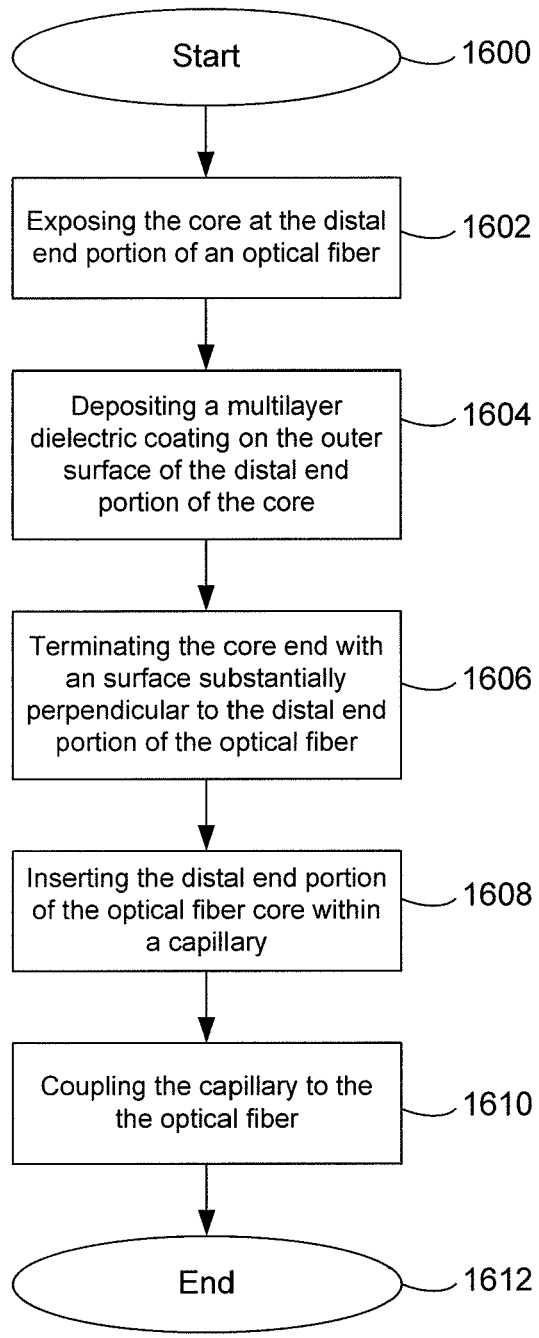

FIG. 18 is a flow chart illustrating a method for manufacturing an end-firing optical fiber, according to another embodiment. At 1602, after start 1600, a distal end portion of an optical fiber core can be exposed by removing a distal end portion of an optical fiber cladding and an optical fiber buffer from an optical fiber. At 1604, a multilayer dielectric coating can be deposited on the outer surface of the distal end portion of the optical fiber core. Placing a multilayer dielectric coating on the outer surface can reduce, for example, the amount of laser energy leakage that can otherwise occur in end-fired operations. At 1606, the distal end portion of the optical fiber core can be terminated with an end surface that is perpendicular to a longitudinal axis or centerline of the distal end portion of the optical fiber core. The end surface can be produced by cleaving and/or polishing the distal end surface of the optical fiber core.

At 1608, the exposed distal end portion of the optical fiber core can be disposed within an inner portion of a capillary. At 1610, a proximal end portion of the capillary can be coupled to the distal end portion of the optical fiber. In one example, the proximal end portion of the capillary and the distal end portion of the optical fiber can be fused together, which may result in an interface or fusion region. Optionally, a cover, such as a metal cap or a low-profile cover, for example, can be deposited on the outer surface of the capillary and/or on the distal end portion of the buffer layer. After 1610, the method can proceed to end 1612.

Figure 19:
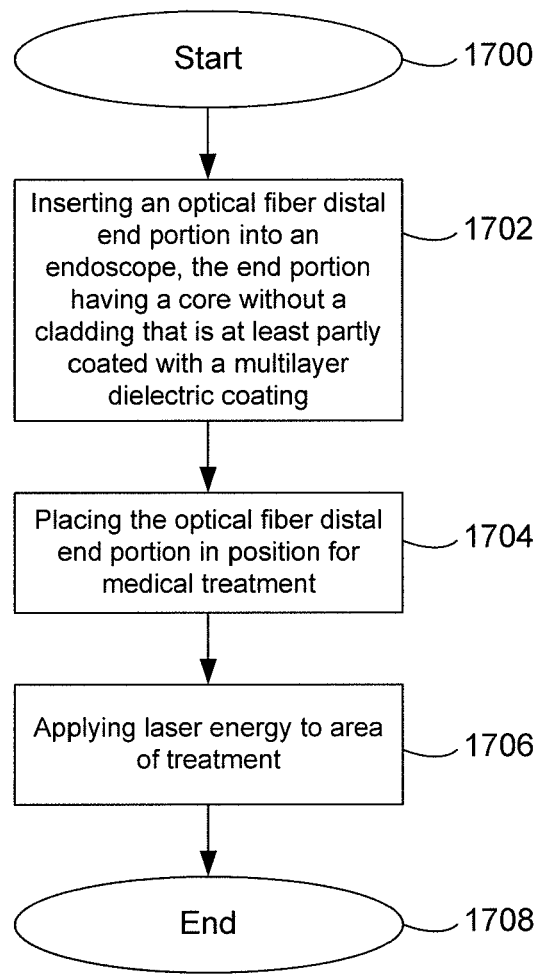

FIG. 19 is a flow chart illustrating a method of using an optical fiber system, according to another embodiment. At 1702, after start 1700, an optical-fiber distal end portion can be inserted within an inner portion or lumen of an elongated member such as, for example, an endoscope. The optical-fiber distal end portion can be a side-firing or an end-firing distal end portion. The optical-fiber distal end portion can include an optical-fiber-core distal end that has the cladding removed and that is disposed within a capillary. The distal end surface of the optical-fiber-core distal end can be an angled surface for side-firing operations or a substantially perpendicular surface for end-firing operations. When the distal end surface is an angled surface, a multilayer dielectric coating can be disposed on the angled surface and/or on a portion of the outer surface of the optical fiber distal end core. When the distal end surface is a substantially perpendicular surface, a multilayer dielectric coating can be disposed on a portion of the outer surface of the optical fiber distal end core.

At 1704, the endoscope can be at least partially inserted into the patient's body during a laser-based surgical procedure. Once inserted into the patient's body, the endoscope can be used to place or position the optical-fiber distal end portion at or near the area of treatment. At 1706, for side-fired surgical procedures, laser energy from a laser source can be transmitted through the optical fiber such that laser energy is side-fired or laterally redirected at the optical-fiber distal end portion for treating a target area. For end-fired surgical procedures, laser energy from a laser source can be transmitted through the optical fiber such that laser energy is end-fired at the optical-fiber distal end portion for treating a target area. After 1706, the method can proceed to end 1708.

While various embodiments have been described above, it should be understood that they have been presented by way of example only, and not limitation. For example, the optical fiber side-firing systems and the optical fiber end-firing systems described herein can include various combinations and/or sub-combinations of the components and/or features of the different embodiments described. Although described with reference to use for treatment of symptoms related to BPH, it should be understood that the optical fiber systems and/or the optical fibers described herein, as well as the methods of using the optical fiber systems and/or the optical fibers described herein, can be used in the treatment of other conditions.

Embodiments of a side-firing optical fiber can also be provided without the optical fiber side-firing system described herein. For example, a side-firing optical fiber can be configured to be used with other laser sources, endoscopes, etc., not specifically described herein. A side-firing optical fiber can have a variety of different shapes and sizes than as illustrated and described herein. A side-firing optical fiber can also include other features and/or components such as, for example, lenses and/or filters.

Embodiments of an end-firing optical fiber can also be provided without the optical fiber end-firing system described herein. For example, an end-firing optical fiber can be configured to be used with other laser sources, endoscopes, etc., not specifically described herein. An end-firing optical fiber can have a variety of different shapes and sizes than as illustrated and described herein. An end-firing optical fiber can also include other features and/or components such as, for example, lenses and/or filters.

What is claimed is:

1. An apparatus, comprising:
   a member having a distal end portion configured to be inserted into a patient's body;
   an optical fiber having a core, a distal end portion of the core having an outer surface terminating at an angled surface that is angled relative to a longitudinal axis of a distal end portion of the optical fiber, the distal end portion of the optical fiber disposed within the member; and
   a multilayer dielectric coating disposed on the angled surface and on a portion of the outer surface extending proximally from the angled surface, the portion of the outer surface being less than the entire circumference of the distal end portion of the core and included opposite a lateral exit of the distal end portion of the core, the multilayer dielectric coating and the angled surface collectively configured to send laser energy from the distal end portion of the core in a direction offset from the longitudinal axis.

2. The apparatus of claim 1, wherein the optical fiber includes a cladding disposed about the core, a distal end portion of the cladding being offset from the distal end portion of the core.

3. The apparatus of claim 1, wherein the optical fiber includes a proximal end portion configured to be coupled to a laser source.

4. The apparatus of claim 1, wherein the multilayer dielectric coating disposed on the angled surface includes a plurality of layers having a first set of layers having an index of refraction and a second set of layers having an index of refraction different than the index of refraction of the first set of layers.

5. The apparatus of claim 1, wherein the member is made of at least one of a sapphire, a ceramic, or a stainless steel.

6. The apparatus of claim 1, wherein the member includes a transmissive portion, the multilayer dielectric coating and the angled surface collectively configured to send laser energy from the distal end portion of the core and through the transmissive portion of the member.

7. The apparatus of claim 1, wherein the member includes a transmissive portion, the distal end portion of the member defining a centerline, the transmissive portion being offset from the centerline.

8. An apparatus, comprising:
   an optical fiber having a core, a distal end portion of the core having an outer surface terminating at an angled surface that is angled relative to a longitudinal axis of a distal end portion of the optical fiber;
   a multilayer dielectric coating disposed on the angled surface and on a portion of the outer surface extending proximally from the angled surface along a length of the distal end portion of the core, the portion of the outer surface being less than the entire circumference of the distal end portion of the core and included opposite a lateral exit of the distal end portion of the core, the multilayer dielectric coating and the angled surface collectively configured to send laser energy from the distal end portion of the core in a direction offset from the longitudinal axis;

wherein the multilayer dielectric coating disposed on the angled surface includes a plurality of layers having a first set of layers having an index of refraction and a second set of layers having an index of refraction different than the index of refraction of the first set of layers; and a capillary member surrounding the distal end portion of the core and including a transmissive portion configured for the passage of laser energy therethrough.

9. The apparatus of claim 8, wherein the optical fiber includes a cladding disposed about the core, a distal end portion of the cladding being offset from the distal end portion of the core.

10. The apparatus of claim 9, wherein the capillary member includes at least one of a sapphire, a ceramic, or a stainless steel.

11. The apparatus of claim 2, further comprising a fusion region between the member and the cladding.

12. The apparatus of claim 9, wherein the cladding is operably coupled to the capillary member via a fusion region.

13. An apparatus, comprising:

a member having a distal end portion configured to be inserted into a patient's body;

an optical fiber having a core, a distal end portion of the core having an outer surface terminating at an angled surface that is angled relative to a longitudinal axis of a distal end portion of the optical fiber, the distal end portion of the optical fiber disposed within the member; and a dielectric coating disposed on the angled surface and on a portion of the outer surface extending proximally from the angled surface, the portion of the outer surface being less than the entire circumference of the distal end portion of the core and included opposite a lateral exit of the distal end portion of the core, the dielectric coating and the angled surface collectively configured to send laser energy from the distal end portion of the core in a direction offset from the longitudinal axis.

* * * * *